United States Patent [19]
Laqua et al.

[11] Patent Number: 5,728,317
[45] Date of Patent: Mar. 17, 1998

[54] POLYISOCYANATE COMPOSITIONS HAVING A LONG SHELF LIFE AND OBTAINABLE BY PHOSGENE-FREE METHODS, THEIR PREPARATION AND THEIR USE

[75] Inventors: Gerhard Laqua, Mannheim; Franz Merger, Frankenthal; Tom Witzel; Ursula Siebenhaar, both of Ludwigshafen; David Agar, Mannheim, all of Germany

[73] Assignee: BASF Aktiengesellschaft, Ludwigshafen, Germany

[21] Appl. No.: 647,877

[22] Filed: May 13, 1996

Related U.S. Application Data

[63] Continuation of Ser. No. 287,564, Aug. 8, 1994, abandoned.

[30] Foreign Application Priority Data

Sep. 13, 1993 [DE] Germany ............... 43 31 083.4

[51] Int. Cl.$^6$ ............ C09K 3/00; C07C 249/00; C07C 251/00; C07C 257/00
[52] U.S. Cl. ............ 252/182.29; 560/330; 560/331; 560/332; 560/333
[58] Field of Search ............ 252/182.29; 560/330, 560/331, 332, 333

[56] References Cited

U.S. PATENT DOCUMENTS

| | | | |
|---|---|---|---|
| 3,247,237 | 4/1966 | Hagemeyer, Jr. | 260/465.9 |
| 4,828,753 | 5/1989 | Robin | 252/182.2 |
| 5,087,739 | 2/1992 | Bohmholdt et al. | 560/345 |
| 5,175,349 | 12/1992 | Gupta et al. | 560/333 |
| 5,258,548 | 11/1993 | Imokawa | 560/333 |
| 5,360,931 | 11/1994 | Bohmholdt et al. | 560/344 |

OTHER PUBLICATIONS

EPO Search Report dated Dec. 27, 1994; Translation of EPO Search Report.

Primary Examiner—Patrick D. Niland
Attorney, Agent, or Firm—Fernando A. Borrego

[57] ABSTRACT

(Cyclo)aliphatic polyisocyanate compositions which have a long shelf life, are obtainable by phosgene-free methods, preferably by thermal cleavage of (cyclo)aliphatic polycarbamates, and, for stabilization, contain at least one primary stabilizer (2a), preferably a sterically hindered phenol and/or an aromatic amine, or at least one secondary stabilizer (2b), preferably an organic phosphite and/or a thioether, or at least one acidic stabilizer (2c), preferably a carboxylic acid, an acyl chloride, an inorganic acid, an inorganic acid chloride and/or a diester of phosphoric acid, or a stabilizer system comprising at least 2 of the stabilizers (2a) to (2c), a process for the preparation of the (cyclo) aliphatic polyisocyanate compositions and their preferred use for the preparation of isocyanurate-containing polyisocyanates.

24 Claims, No Drawings

POLYISOCYANATE COMPOSITIONS HAVING A LONG SHELF LIFE AND OBTAINABLE BY PHOSGENE-FREE METHODS, THEIR PREPARATION AND THEIR USE

This is a continuation of U.S. Pat. application Ser. No. 08/287,564, filed Aug. 8, 1994 now abandoned.

Polyisocyanate compositions which are obtainable by phosgene-free methods, preferably by thermal cleavage of (cyclo)aliphatic poly-carbamates, are stabilized by the addition of at least one stabilizer selected from the group consisting of primary stabilizers (2a) as a free radical acceptor and/or antioxidant, one secondary stabilizer (2b) as a peroxide cleaver and/or reducing agent and one acidic stabilizer (2c) as a moderator or of a stabilizer system comprising at least one primary (2a) and at least one acidic stabilizer (2c) or at least one primary (2a), at least one secondary (2b) and at least one acidic stabilizer (2c).

Organic polyisocyanates, for example aromatic, cycloaliphatic and aliphatic difunctional and polyfunctional polyisocyanates, can be prepared by various processes (Annalen der Chemie 562 (1949), 75 et seq.). The preparation of organic polyisocyanates by phosgenation of polyamines to give the corresponding polycarbamoyl chlorides and the thermal cleavage thereof into organic polyisocyanates and hydrogen chloride has proven technically particularly useful, so that at present only this preparation process is used industrially.

The high conversion of chlorine via phosgene and carbamoyl chloride into hydrogen chloride, the toxicity of the phosgene and the associated expensive safety precautions, the corrosiveness of the reaction mixture, the instability of the solvents usually used and the formation of chlorine-containing and chlorine-free by-products, which play a decisive role in determining the physical properties, for example the color, the viscosity and the vapor pressure, and chemical properties, for example reactivity, shelf life, etc., of the polyisocyanates and the mechanical properties of the polyisocyanate polyadducts prepared from such polyisocyanates, present problems in this procedure.

There has therefore been no lack of attempts to prepare organic, preferably aromatic polyisocyanates without the use of phosgene, ie. by phosgene-free methods.

According to EP-B-0 126 299 (U.S. Pat. No. 4,596,678), EP-B-0 126 300 (U.S. Pat. No. 4,596,679) and EP-A-0 355 443 (U.S. Pat. No. 5,087,739), (cyclo)aliphatic diisocyanates, such as hexamethylene 1,6-diisocyanate (HDI), and/or isomeric aliphatic diisocyanates where the alkylene radical is of 6 carbon atoms and 1-isocyanato-3-isocyanato-methyl-3,5,5-trimethylcyclohexane (isophorone diisocyanate or IPDI) can be prepared by circulation processes, by reacting the (cyclo)aliphatic diamines with urea and alcohols and, if required, N-unsubstituted carbamates, dialkyl carbonates and other by-products recycled from the reaction process to give (cyclo)aliphatic biscarbamates and subjecting the latter to thermal cleavage to give the corresponding diisocyanates and alcohols.

Depending on the type of preparation process, the organic polyisocyanates contain different by-products having an unknown structure in many cases, the chlorine-containing by-products particularly influencing the shelf life, reactivity and color of the composition.

According to U.S. Pat. No. 3,330,849, for example, organic polyisocyanates can be stabilized to discoloration and precipitate formation by adding sulfonyl isocyanates. According to U.S. Pat. No. 3,373,182, the hydrolyzable chlorine content of isocyanates can be reduced by adding metal naphthenates, for example cadmium, cobalt, copper, lead, manganese or zinc naphthenate. U.S. Pat. No. 3,384,653 and U.S. Pat. No. 3,449,256 describe the improvement of the shelf life of diphenylmethane 4,4'-diisocyanate by treatment at from 160° to 250° C. with trialkyl phosphates. According to U.S. Pat. No. 3,458,558, the content of hydrolyzable chlorine compounds can be reduced in the case of organic isocyanates also with copper, silver, nickel, iron and zinc at above 100° C. According to U.S. Pat. No. 3,479,393, trialkylaminoboranes stabilize isocyanates to discoloration. According to U.S. Pat. No. 3,535,359, ortho-carboxylates are suitable for stabilizing organic isocyanates to an increase in viscosity. According to U.S. Pat. No. 3,585,229, polyisocyanate mixtures containing diphenylmethane diisocyanate can be decolorized by adding diphenyl decyl phosphite. According to U.S. Pat. No. 3,692,813, organic polyisocyanates can be stabilized to decomposition with the aid of oxycarbonyl isocyanates having at least one group of the formula —O—CO—NCO. According to U.S. Pat. No. 3,715,381, 2,6-di-tert-butyl-p-cresol can be used for stabilizing organic polyisocyanates to discoloration. According to U.S. Pat. No. 3,970,680, diphenylmethane diisocyanates can also be stabilized by adding tertiary amines. According to U.S. Pat. No. 4,065,362, organic isocyanates can be purified by treatment at above 100° C. with a metal salt of mercaptobenzothiazole, a metal salt of an alkyl-substituted dithiocarbamic acid, an alkyl-substituted phenol, a thiobisphenol or a triaryl phosphite. According to U.S. Pat. No. 3,247,236, diisocyanates prepared by reacting diamines with phosgene and purified by distillation can be stabilized by adding carbon dioxide or sulfur dioxide. The good solubility of the sulfur dioxide in the polyisocyanate and the resulting discoloration during storage are disadvantages of this process. The stated patent publications provide no information about the stabilization of organic polyisocyanates prepared by phosgene-free methods, preferably by thermal cleavage of organic polycarbamates.

(Cyclo)aliphatic polyisocyanates obtainable by phosgene-free methods, in particular by thermal cleavage of (cyclo)aliphatic polycarbamates, do not have a long shelf life. Their instability is due to the lack of hydrolyzable chlorine compounds and to the presence of catalytic impurities of unknown structure which promote, for example, the formation of oligomers. At low temperatures for example at +5° C. or lower for example hexamethylene diisocyanate (HDI) tends to form linear HDI oligomers of the formula

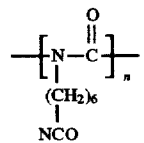

The molecular weight increase associated with an increase in viscosity may lead to gelling of the polyisocyanate, for example of HDI. Such products are difficult to handle, can no longer be reproducibly converted into polyisocyanate polyadducts and must therefore be discarded. At higher storage temperatures, for example, the reactivity of the HDI prepared by the phosgene-free method decreases sharply, particularly in the case of the trimerization reaction catalyzed with quaternary ammonium hydroxide compounds. Isocyanurate-containing polyisocyanates which have an intense color and in particular can no longer be used as a coating raw material are obtained.

It is an object of the present invention to use suitable measures to stabilize organic, preferably (cyclo)aliphatic polyisocyanates prepared by phosgene-free methods, without adversely affecting the reactivity of the polyisocyanates. The oligomerization of the polyisocyanates and an increase in the viscosity of the polyisocyanate composition as well as their discoloration during storage are to be prevented.

We have found that this object is achieved, surprisingly, by the addition of stabilizers known per se.

The present invention therefore relates to organic, preferably (cyclo)aliphatic, polyisocyanate compositions which have a long shelf life and contain or preferably consist of
1) a polyisocyanate prepared by a phosgene-free method, preferably a (cyclo)aliphatic polyisocyanate obtainable by thermal cleavage of (cyclo)aliphatic polycarbamates and
2) a stabilizer selected from the group consisting of
    2a) primary stabilizers or
    2b) secondary stabilizers or
    2c) acidic stabilizers or
3) a stabilizer system comprising
    at least one primary (2a) and
    at least one acidic stabilizer (2c) or
    at least one primary (2a), at least one secondary (2b) and at least one acidic stabilizer (2c).

The present invention furthermore relates to a process, as claimed in any of claims 10 to 12, for improving the stability of polyisocyanate compositions obtainable by phosgene-free methods, preferably by thermal cleavage of (cyclo)aliphatic polycarbamates, and the preferred use of the novel stable (cyclo)aliphatic polyisocyanate compositions for the preparation of isocyanurate-containing polyisocyanates as claimed in claim 13.

Although the spectrum of by-products of polyisocyanates obtainable by thermal cleavage of carbamoyl chlorides and of polyisocyanates obtainable by phosgene-free methods, preferably by thermal cleavage of carbamates, differs considerably, it was surprisingly possible, by adding the conventional stabilizers effective in the presence of chlorine-containing by-products, also to stabilize the reactivity and color number of (cyclo)aliphatic polyisocyanates prepared by phosgene-free methods. The novel (cyclo)aliphatic polyisocyanate compositions have a long shelf life under the conventional storage conditions, for example at from −20° to +40° C., ie. their physical and chemical characteristics are essentially constant.

The novel polyisocyanate compositions may contain any (cyclo)aliphatic polyisocyanates, with the proviso that they have been prepared by suitable methods in the absence of phosgene. (Cyclo)aliphatic polyisocyanates which are obtainable by thermal cleavage of (cyclo)aliphatic polycarbamates are very suitable and are therefore preferably used. Useful aliphatic polyisocyanates advantageously have 3 to 16, preferably 4 to 12, carbon atoms in the linear or branched alkylene radical and suitable cycloaliphatic polyisocyanates advantageously have 4 to 18, preferably 6 to 15, carbon atoms in the cycloalkylene radical. Examples are 1,4-diisocyanatobutane, 2-ethyl-1,4-diisocyanatobutane, 1,5-diisocyanatopentane, 2-methyl-1,5-diisocyanatopentane, 2,2-dimethyl-1,5-diisocyanatopentane, 2-ethyl-2-propyl-1,5-diisocyanatopentane, 2-ethyl-2-butyl-1,5-diisocyanatopentane, 2-alkoxymethylene-1,5-diisocyanatopentane, hexamethylene 1,6-diisocyanate, 2,4, 4- and 2,2,4-trimethylhexamethylene 1,6-diisocyanate, 1,7-diisocyanatoheptane, 1,8-diisocyanatooctane, 1,10-diisocyanatodecane, 1,12-diisocyanatododecane, 4,4'-diisocyanatodicyclohexylmethane, 2,4'-diisocyanatodicyclohexylmethane and mixtures of the diisocyanatodicyclohexylmethane isomers, 1,3-diisocyanatocyclohexane and isomer mixtures of diisocyanatocyclohexanes and 1-isocyanato-3-isocyanatomethyl-3,5,5-trimethylcyclohexane. Preferably used (cyclo)aliphatic polyisocyanates are hexamethylene 1,6-diisocyanate, isomeric aliphatic diisocyanates having 6 carbon atoms in the alkylene radical and mixtures thereof and 1-isocyanato-3-isocyanatomethyl-3,5,5-trimethylcyclohexane.

As has already been described, the (cyclo)aliphatic diisocyanates are preferably prepared by thermal cleavage of the corresponding dicarbamates. This cleavage may be carried out, for example, at from 150° to 300° C., preferably from 180° to 250° C., and from 0.001 to 2 bar, preferably from 1 to 200 mbar, in the absence or, preferably, in the presence of catalysts in suitable cleavage reactors, for example thin-film evaporators or preferably heating-element evaporators, according to EP-A-0 524 554. The diisocyanates and alcohols formed in the cleavage can be separated, for example, by fractional condensation or preferably by rectification and the diisocyanates can be additionally purified, for example, by distillation.

Compounds which are usually effective as antioxidants and/or free radical acceptors are advantageously used as primary stabilizers (2a) for stabilizing the (cyclo)aliphatic polyisocyanates obtainable by phosgene-free methods, preferably those obtainable by thermal cleavage of (cyclo) aliphatic polycarbamates. Suitable primary stabilizers (2a) for the purposes of the present invention are preferably phenolic antioxidants, ie. compounds which contain at least one sterically hindered phenolic group. Examples of phenolic antioxidants are 2,6-di-tert-butyl-4-methylphenol, 2,4,6-tri-tert-butylphenol, 2,2'-methylenebis-(4-methyl-6-tert-5 butylphenol), 2,2'-thiobis-(4-methyl-6-tert-butylphenol), 4,4'-thiobis-(S-methyl-6-tert-butylphenol), 4,4'-butylidene-bis-(6-tert-butyl-3-methylphenol), 4,4'-methylidenebis-(2,6-di-tert-butylphenol), 2,2'-methylenebis-[4-methyl-6-(1-methylcyclohexyl)-phenol], tetrakis-[methylene-3-(3,5-di-tert-butyl-4-hydroxyphenyl)-propionyl]-methane, 1,3,5-trimethyl-2,4,6-tris-(3,5-di-tert-butyl-4-hydroxybenzyl)-benzene, N,N'-hexamethylene-bis-(3,5-di-tert-butyl-4-hydroxyhydrocinnamide), octadecyl 3-(3,5-di-tert-butyl-4-hydroxyphenyl)-propionate, 1,3,5-tris-(3,5-di-tert-butyl-4-hydroxybenzyl) isocyanurate, 1,1,3-tris-(5-tert-butyl-4-hydroxy-2-methylphenyl)-butane, 1,3,5-tris-(3,5-di-tert-butyl-4-hydroxybenzyl)-mesitylene, ethylene glycol bis-(3,3-bis-(3'-tert-butyl-4'-hydroxyphenyl)-butyrate], 2,2'-thiodiethyl bis-3-(3,5-di-tert-butyl-4-hydroxyphenyl)-propionate, di-(3-tert-butyl-4'-hydroxy-5-methylphenyl)-dicyclopentadiene, 2,2'-methylenebis-(4-methyl-6-cyclohexylphenol), 1,6-hexanediol bis-(3,5-di-tert-butyl-4-hydroxyphenyl)-propionate, 2,4-bis-(n-octylthio)-6-(4-hydroxy-3,5-di-tert-butylanilino)-1,3,5-triazine, diethyl 3,5-di-tert-butyl-4-hydroxybenzylphosphonate and triethylene glycol bis-3-(tert-butyl-4-hydroxy-5-methylphenyl)-propionate.

For example, octadecyl 3-(3,5-di-tert-butyl-4-hydroxyphenyl)-propionate, 2,2'-methylenebis-(4-methyl-6-cyclohexylphenol), 2,2'-methylenebis-(4-methyl-6-tert-butylphenol), triethylene glycol bis-3-(tert-butyl-4-hydroxy-5-methylphenyl)-propionate, tetrakis-[methylene-3-(3,5-di-tert-butyl-4-hydroxyphenyl)-propionyl]-methane and in particular 2,6-di-tert-butyl-4-methylphenol and 3,5-di-tert-butyl-4-hydroxyanisole have proven very suitable and are therefore preferably used.

Nitrogen-containing stabilizers, preferably aromatic amines substituted by alkyl, cycloalkyl and/or aryl radicals, for example 4,4'-di-tert-octyldiphenylamine, 4,4'-di-(α,α-dimethylbenzyl)-diphenylamine, phenyl-β-naphthylamine, N-isopropyl-N'-phenyl-p-phenylenediamine, N-phenyl-2-naphthylamine and/or phenyl-2-amino-naphthalene, may furthermore be used as primary stabilizers (2a).

The sterically hindered phenols and aromatic amines may each be used individually or in the form of mixtures. Mixtures of at least one sterically hindered phenol and at least one aromatic amine may also be used.

The primary stabilizers (2a) are advantageously used in an amount of from 1 to 1000, preferably from 20 to 500, in particular from 50 to 100, ppm, based on the weight of the polyisocyanate composition.

Compounds which are usually effective as peroxide-cleaving and/or reducing agents are advantageously used as secondary stabilizers (2b), which may be employed as sole stabilizers or, preferably, together with the primary stabilizers (2a). Suitable secondary stabilizers (2b) for the purposes of the present invention are, for example, phosphorus-containing compounds, preferably triesters of phosphorous acid, for example trialkyl phosphites and triaryl phosphites, and thioethers.

Esters of phosphorous acid, eg. distearyl pentaerythrityl diphosphite, tris-(nonylphenyl) phosphite, tetrakis-(2,4-di-tert-butylphenyl-4,4'-biphenylene) diphosphonite, tris-(2,4-di-tert-butylphenyl) phosphite, neopentylglycol triethylene glycol diphosphite, diisodecyl pentaerythrityl diphosphite, tristearyl phosphite, trilauryl phosphite and triphenyl phosphite, which is preferably used, have proven useful as secondary stabilizers.

Examples of suitable thioethers are 2-methyl-1-propenyl tert-dodecyl thioether, cyclohexylidenemethyl n-dodecyl thioether, 3-cyclohexen-1-ylidenemethyl n-octadecyl thioether, 3-cyclohexen-1-ylidenemethyl n-dodecyl thioether, 3-cyclohexen-1-ylidenemethyl n-octyl thioether, 3-cyclohexen-1-ylidenemethyl cyclohexyl thioether, 3-methyl-3-cyclohexen-1-ylidenemethyl n-dodecyl thioether, 3-cyclohexen-1-ylidenemethyl p-tolyl thioether, 3-cyclohexen-1-ylidenemethyl benzyl thioether and preferably 3-cyclohexen-1-ylidenemethyl n-dodecyl thioether and 1-hexenyl n-dodecyl thioether.

The secondary stabilizers (2b) which are suitable according to the invention and are selected from the group consisting of the organic phosphites and thioethers, as well as the primary stabilizers (2a), may each be used individually or as a mixture with one another. However, mixtures of at least one organic phosphite and at least one thioether may also be used.

If exclusively secondary stabilizers are used for stabilizing the (cyclo)aliphatic polyisocyanate compositions, said stabilizers are advantageously employed in an amount of from 1 to 1000, preferably from 20 to 500, in particular from 50 to 100, ppm, based on the weight of the polyisocyanate composition.

The (cyclo)aliphatic polyisocyanate compositions can be very well stabilized for at least 2 months at 45° C. simply by the addition of the primary stabilizers (2a) which act, for example, as antioxidants, such as the sterically hindered phenols. However, if the polyisocyanate compositions come into contact with air to a relatively great extent, it may be necessary to increase the added amounts of, for example, sterically hindered phenols to such an extent that the limit of 1000 ppm is reached or is even exceeded. However, since large amounts of sterically hindered phenols may not only stabilize the reactivity but also increase it, it cannot be ruled out, finally, that gel formation of the (cyclo)aliphatic polyisocyanates may be forced under certain currently still unknown conditions. Particularly under these preconditions, the addition of secondary stabilizers, preferably of trialkyl and/or triaryl phosphites, has proven extremely advantageous. As a result of the addition of the secondary stabilizers (2b) having a reducing effect, it is therefore possible to counteract an unforeseeable increase in reactivity. Moderately reactive (cyclo)aliphatic polyisocyanate compositions or individual batches of not completely on-spec product can be excellently stabilized with binary stabilizer systems comprising primary and secondary stabilizers and therefore used industrially.

Highly reactive (cyclo)aliphatic polyisocyanates or individual batches having a differing increased reactivity can be stabilized by the addition of acidic stabilizers (2c). The acidic stabilizers reduce the reactivity and may suppress unintentional oligomerization during storage. The fact that polyisocyanate compositions stabilized in this manner can be trimerized without an increase in the color number is also advantageous.

Examples of suitable acidic stabilizers (2c) are organic monocarboxylic acids and/or organic polycarboxylic acids, for example linear or branched aliphatic monocarboxylic acids of 1 to 12, preferably 1 to 8, carbon atoms which may be substituted by halogen, preferably chlorine and/or alkoxy of 1 to 12, preferably 1 to 6, carbon atoms, in particular methoxy and/or ethoxy, eg. formic acid, acetic acid, propionic acid, 2,2-dimethylpropionic acid, butyric acid, isobutyric acid, 2-methoxybutyric acid, n-valeric acid, chloroacetic acid, caproic acid, 2-ethylhexanoic acid, n-heptanoic acid, n-octanoic acid, caprylic acid and pelargoic acid, aromatic monocarboxylic acids of 6 to 12 carbon atoms, eg. benzoic acid, toluic acid and naphthenic acid, aliphatic polycarboxylic acids of 2 to 12, preferably 4 to 6, carbon atoms, eg. oxalic acid, succinic acid, maleic acid, fumaric acid, 2-ethylsuccinic acid, glutaric acid, 2-methylglutaric acid, adipic acid, 2-methyl- and 2,2-dimethyladipic acid, 1,8-octanoic acid, 1,10-decanoic acid and 1,12-dodecanoic acid, aromatic dicarboxylic acids of 8 to 12 carbon atoms, eg. phthalic acid, terephthalic acid and isophthalic acid, acyl chlorides, for example aliphatic and aromatic monoacyl chlorides, acyl mono- and dichlorides of aliphatic and aromatic polycarboxylic acids, preferably dicarboxylic acids, inorganic acids, such as phosphoric acid, phosphorous acid and hydrochloric acid, and diesters, for example the alkyl and/or aryl diesters of phosphoric acid and/or phosphorous acid, or inorganic acid chlorides, such as phosphoryl chloride or thionyl chloride. The acidic stabilizers may be used individually or in the form of a mixture of at least two acidic stabilizers. Preferably used acidic stabilizers are aliphatic monocarboxylic acids of 1 to 8 carbon atoms, eg. formic acid, acetic acid and in particular 2-ethylhexanoic acid, and aliphatic dicarboxylic acids of 2 to 6 carbon atoms, eg. oxalic acid.

If the acidic stabilizers (2c), which may also be referred to as moderators, are used alone for stabilizing the (cyclo)aliphatic polyisocyanates prepared by phosgene-free methods, they are advantageously used in an amount of from 1 to 1000, preferably from 20 to 500, in particular from 50 to 100, ppm, based on the weight of the polyisocyanate composition.

As stated above, the primary, secondary and acidic stabilizers which can be used according to the invention may be employed individually for stabilizing the polyisocyanates obtainable by phosgene-free methods, preferably by thermal cleavage of (cyclo)aliphatic polycarbamates. Owing to the different spectrum of by-products and the amounts thereof, it has however proven advantageous to use stabilizer systems comprising at least 2 of the stabilizers (2a) to (2c). Suitable stabilizer systems can be determined theoretically and/or experimentally on the basis of the physical properties and of a chemical analysis of the (cyclo)aliphatic polyisocyanates. Stabilizer systems which contain, or preferably consist of, at least one primary (2a) and at least one acidic stabilizer (2c) or at least one primary (2a), at least one secondary (2b) and at least one acidic stabilizer (2c) are preferably used. Such stabilizer systems advantageously contain from 1 to 1000, preferably from 20 to 500, in particular from 50 to 100, ppm of the primary stabilizer (2a), from 0 to 1000, preferably from 1 to 1000, in particular from 50 to 100, ppm of the secondary stabilizer (2b) and from 0 to 1000, preferably from 1 to 1000, in particular from 50 to 100, ppm of the acidic stabilizer (2c), the amounts being based on the weight of the polyisocyanate composition. Stabilizer systems which contain a sterically hindered phenol, in particular 2,6-di-tert-butyl-4-methylphenol, as the primary stabilizer (2a), an organic phosphite, in particular triphenyl phosphite, as the secondary stabilizer and an organic carboxylic acid, in particular 2-ethylhexanoic acid, as the acidic stabilizer (2c) have proven very suitable and are therefore preferably used.

For the preparation of the novel (cyclo)aliphatic polyisocyanate composition having improved stability, stabilizers (2a) to (2c) may be incorporated in the (cyclo)aliphatic polyisocyanates in the required, effective amount, individually, in succession or simultaneously, in solid form or as a solution, dispersion and/or emulsion. The stabilizers are advantageously added at from −10° to 50° C., preferably from 20° to 40° C., expediently while stirring the (cyclo)aliphatic polyisocyanates.

The novel (cyclo)aliphatic polyisocyanate compositions have a shelf life of more than 12 weeks. They may be converted directly into polyisocyanate polyadducts or into modified polyisocyanates, for example into polyisocyanates modified with urethane, allophanate, uretonimine, carbodiimide and/or biuret groups. The polyisocyanate compositions stabilized according to the invention are preferably used for the preparation of isocyanurate-containing polyisocyanates.

EXAMPLES

Example 1

100 mol ppm of 2,6-di-tert-butyl-4-methylphenol were added, while stirring at 23° C., to a hexamethylene 1,6-diisocyanate (HDI) prepared by thermal decomposition of 1,6-hexamethylenedibutylurethane, and the mixture was stored in a V2A stainless steel container under nitrogen at 45° C. for 70 days.

Comparative Example I

A part of the abovementioned HDI was stored under the same conditions but in the absence of a stabilizer.

Preparation of Isocyanurate-containing Polyisocyanate Mixtures

The abovementioned HDIs were trimerized in the presence of 500 ppm of N,N,N-trimethyl-N-(2-hydroxypropyl)-ammonium 2-ethyl-hexanoate at 80° C. while stirring. After a reaction time of one hour, the reaction was stopped by adding dibutyl phosphate.

The following properties of the reaction mixtures were measured:

|  | Example 1 | Comparative Example I |
|---|---|---|
| HDI content after storage [% by weight] | 97.2 | 98.2 |
| Remaining components to 100% by weight: | Oligomers | Oligomers |
| NCO content of the reaction mixture after trimerization [% by weight] | 36.8 | 43.9 |
| Hazen color number of the reaction mixture after trimerization | 54 | 316 |

The unstabilized HDI of Comparative Example I has a lower reactivity which contributes to a lower conversion and substantially poorer color number in the formation of the isocyanurate-containing polyisocyanate mixture.

Example 2

100 mol ppm of 2,6-di-tert-butyl-4-methylphenol and 500 mol ppm of triphenyl phosphite were added, while stirring at 23° C., to a hexamethylene 1,6-diisocyanate prepared by thermal decomposition of 1,6-hexamethylenedibutylurethane, and the mixture was stored in a V2A stainless steel container under nitrogen at 45° C. for 80 days.

Comparative Example II

A part of the abovementioned HDI was stored under the same conditions but in the absence of a stabilizer.

The preparation of isocyanurate-containing polyisocyanate mixtures was carried out similarly to Example 1 and Comparative Example I.

The following properties of the reaction mixtures were measured:

|  | Example 2 | Comparative Example II |
|---|---|---|
| HDI content after storage [% by weight] | 95.9 | 98.2 |
| Remaining components to 100% by weight: | Oligomers | Oligomers |
| NCO content of the reaction mixture after trimerization [% by weight] | 38.2 | 41.5 |
| Hazen color number of the reaction mixture after trimerization | 35 | 256 |

Example 3

500 mol ppm of 2-ethylhexanoic acid were added, while stirring at 23° C., to a hexamethylene 1,6-diisocynanate prepared by thermal decomposition of 1,6-hexamethylenedibutylurethane, and the mixture was stored in a V2A stainless steel container under nitrogen at 45° C. for 60 days.

Comparative Example III

A part of the abovementioned HDI was stored under the same conditions but in the absence of a stabilizer.

The preparation of isocyanurate-containing polyisocyanate mixtures was carried out similarly to Example 1 and Comparative Example I.

The following properties of the reaction mixtures were measured:

|  | Example 3 | Comparative Example III |
|---|---|---|
| HDI content after storage [% by weight] | 98.7 | 97.7 |
| Remaining components to 100% by weight: | Oligomers | Oligomers |
| NCO content of the reaction mixture after trimerization [% by weight] | 38.0 | 40.0 |
| Hazen color number of the reaction mixture after trimerization | 162 | 220 |

As a result of the addition of stabilizers, oligomer formation during storage is reduced and an isocyanurate-containing polyisocyanate mixture having a substantially improved color number is obtained. The HDI reactivity is not adversely affected by the stabilizer.

Example 4

100 mol ppm of 2,6-di-tert-butyl-4-methylphenol and 100 mol ppm of 2-ethylhexanoic acid were added, while stirring at 23° C., to a hexamethylene 1,6-diisocyanate prepared by thermal decomposition of 1,6-hexamethylenedibutylurethane, and the mixture was stored in a V2A stainless steel container under nitrogen at 45° C. for 47 days.

Comparative Example IV

A part of the abovementioned HDI was stored under the same conditions but in the absence of a stabilizer.

The preparation of isocyanurate-containing polyisocyanate mixtures was carried out similarly to Example I and Comparative Example I.

The following properties of the reaction mixtures were measured:

|  | Example 4 | Comparative Example IV |
|---|---|---|
| HDI content after storage [% by weight] | 98.2 | 98.2 |
| Remaining components to 100% by weight: | Oligomers | Oligomers |
| NCO content of the reaction mixture after trimerization [% by weight] | 35.9 | 40.0 |
| Hazen color number of the reaction mixture after trimerization | 55 | 143 |

The reactivity of the HDI and the color number in the isocyanurate formation is stabilized by the stabilizer combination.

Example 5

100 mol ppm of 2,6-di-tert-butyl-4-methylphenol, 500 mol ppm of triphenyl phosphite and 100 mol ppm of 2-ethylhexanoic acid were added, while stirring at 23° C., to a hexamethylene 1,6-diisocyanate prepared by thermal decomposition of 1,6-hexamethylenedibutylurethane, and the mixture was stored in a V2A stainless steel container under nitrogen at 45° C. for 80 days.

Comparative Example V

A part of the abovementioned HDI was stored under the same conditions but in the absence of a stabilizer.

The preparation of isocyanurate-containing polyisocyanate mixtures was carried out similarly to Example 1 and Comparative Example I.

The following properties of the reaction mixture were measured:

|  | Example 5 | Comparative Example V |
|---|---|---|
| HDI content after storage [% by weight] | 98.7 | 98.2 |
| Remaining components to 100% by weight: | Oligomers | Oligomers |
| NCO content of the reaction mixture after trimerization [% by weight] | 37.9 | 41.5 |
| Hazen color number of the reaction mixture after trimerization | 39 | 256 |

The stabilizer combination stabilizes the reactivity and color number of the HDI in the isocyanurate formation. Oligomer formation during storage is reduced.

We claim:

1. A stable cycloaliphatic or aliphatic polyisocyanate composition containing
   1) a cycloaliphatic or aliphatic polyisocyanate prepared by a phosgene-free method and
   2) a stabilizer selected from the group consisting of
      2a) primary stabilizers selected from the group consisting of antioxidants, free radical acceptors, nitrogen-containing stabilizer compounds and mixtures thereof, or
      2b) secondary stabilizers selected from the group consisting of peroxide cleaving agents, reducing agents and mixtures thereof, or
      2c) acidic stabilizers selected from the group consisting of monocarboxylic acids, organic polycarboxylic acids, inorganic acids, diester of phosphoric acid, diester of phosphorous acid, acyl chlorides, inorganic acid chlorides and mixtures thereof,
   3) wherein at least one primary stabilizer (2a) and at least one acidic stabilizer (2c) are employed.

2. A stable cycloaliphatic or aliphatic polyisocyanate composition containing
   1) a cycloaliphatic or aliphatic polyisocyanate obtained by thermal cleavage of cycloaliphatic or aliphatic polycarbamates and
   2) a stabilizer selected from the group consisting of
      2a) primary stabilizers selected from the group consisting of antioxidants, free radical acceptors, nitrogen-containing stabilizer compounds and mixtures thereof, or
      2b) secondary stabilizers selected from the group consisting of peroxide cleaving agents, reducing agents and mixtures thereof, or
      2c) acidic stabilizers selected from the group consisting of monocarboxylic acids, organic polycarboxylie acids, inorganic acids, diester of phosphoric acid, diester of phosphorous acid, acyl chlorides, inorganic acid chlorides and mixtures thereof,
   3) wherein at least one primary stabilizer (2a) and at least one acidic stabilizer (2c) are employed.

3. A stable cycloaliphatic or aliphatic polyisocyanate composition as claimed in claim 1, containing, as primary stabilizers (2a), at least one sterically hindered phenol, at least one aromatic amine or a mixture of at least one sterically hindered phenol and at least one aromatic amine.

4. A stable (cyclo)aliphatic polyisocyanate composition as claimed in claim 1, containing, as secondary stabilizers (2b), at least one organic phosphite, at least one thioether or a mixture of at least one organic phosphite and at least one thioether.

5. A stable (cyclo)aliphatic polyisocyanate composition as claimed in claim 1, containing, as acidic stabilizers (2c), at least one organic monocarboxylic acid, at least one organic polycarboxylic acid, at least one inorganic acid, at least one diester of phosphoric acid or of phosphorous acid, at least one acyl chloride or at least one inorganic acid chloride or a mixture of at least 2 of the stated acidic stabilizers.

6. A stable (cyclo)aliphatic polyisocyanate composition as claimed in claim 1 containing
   2a) from 1 to 1000 ppm of at least one primary stabilizer (2a) or
   2b) from 1 to 1000 ppm of at least one secondary stabilizer (2b) or
   2c) from 1 to 1000 ppm of at least one acidic stabilizer (2c) or
   3) a stabilizer system comprising
      from 1 to 1000 ppm of (2a),
      from 0 to 1000 ppm of (2b) and
      from 0 to 1000 ppm of (2c),
   the amounts being based on the weight of the polyisocyanate composition.

7. A stable (cyclo)aliphatic polyisocyanate composition as claimed in claim 1, containing
   2a) 2,6-di-tert-butyl-4-methylphenol as the primary stabilizer,
   2b) triphenyl phosphite as the secondary stabilizer and
   2c) 2-ethylhexanoic acid as the acidic stabilizer.

8. A stable (cyclo)aliphatic polyisocyanate composition as claimed in claim 1, containing hexamethylene 1,6-diisocyanate as the aliphatic polyisocyanate (1).

9. A stable (cyclo)aliphatic polyisocyanate composition as claimed in claim 1, containing 1-isocyanato-3-isocyanatomethyl-3,5,5-trimethylcyclohexane as the cycloaliphatic polyisocyanate (1).

10. A process for improving the stability of cycloaliphatic or aliphatic polyisocyanate compositions obtained by a phosgene-free method, wherein a stabilizer selected from the group consisting of primary stabilizers (2a) selected from the group consisting of antioxidants, free radical acceptors, nitrogen-containing stabilizer compounds and mixtures thereof, or secondary stabilizers (2b) selected from the group consisting of peroxide cleaving agents, reducing agents and mixtures thereof, or acidic stabilizers (2c) selected from the group consisting of monocarboxylic acids, organic polycarboxylic acids, inorganic acids, diester of phosphoric acid, diester of phosphorous acid, acyl chlorides, inorganic acid chlorides and mixtures thereof, wherein at least one primary stabilizer (2a) and at least one acidic stabilizer (2c) is incorporated in an effective amount in said compositions.

11. A process as claimed in claim 10, wherein the cycloaliphatic or aliphatic polyisocyanate compositions contain (cyclo)aliphatic polyisocyanates obtained by thermal cleavage of (cyclo)aliphatic polycarbamates.

12. A process as claimed in claim 10 wherein
   from 1 to 1000 ppm of at least one primary stabilizer (2a) or
   from 1 to 1000 ppm of at least one secondary stabilizer (2b) or
   from 1 to 1000 ppm of at least one acidic stabilizer (2c) or a stabilizer system comprising
      from 1 to 1000 ppm of (2a),
      from 0 to 1000 ppm of (2b) and
      from 0 to 1000 ppm of (2c)
   is incorporated in the (cyclo)aliphatic polyisocyanate compositions.

13. A stable cycloaliphatic or aliphatic polyisocyanate composition as claimed in claim 2, containing, as primary stabilizers (2a), at least one sterically hindered phenol, at least one aromatic amine or a mixture of at least one sterically hindered phenol and at least one aromatic amine.

14. A stable (cyclo) aliphatic polyisocyanate composition as claimed in claim 2, containing, as secondary stabilizers (2b), at least one organic phosphite, at least one thioether or a mixture of at least one organic phosphite and at least one thioether.

15. A stable (cyclo) aliphatic polyisocyanate composition as claimed in claim 2, containing, as acidic stabilizers (2c), at least one organic monocarboxylic acid, at least one organic polycarboxylic acid, at least one inorganic acid, at least one diester of phosphoric acid or of phosphorous acid, at least one acyl chloride or at least one inorganic acid chloride or a mixture of at least two of the stated acidic stabilizers.

16. A stabile (cyclo) aliphatic polyisocyanate composition as claimed in claim 2, containing
   2a) from 1 to 1000 ppm of at least one primary stabilizer (2a) or
   2b) from 1 to 1000 ppm of at least one secondary stabilizer (2b) or
   2c) from 1 to 1000 ppm of at least one acidic stabilizer (2c) or
   3) a stabilizer system comprising
      from 1 to 1000 ppm of (2a),
      from 0 to 1000 ppm of (2b), and
      from 0 to 1000 ppm of (2c),
   the amounts being based on the weight of the polyisocyanate composition.

17. A stable (cyclo) aliphatic polyisocyanate composition as claimed in claim 2, containing
   2a) 2,6-di-tert-butyl-4-methylphenol as the primary stabilizer,
   2b) triphenyl phosphite as the secondary stabilizer and
   2c) 2-ethylhexanoic acid as the acidic stabilizer.

18. A stable (cyclo) aliphatic polyisocyanate composition as claimed in claim 2, containing hexamethylene 1,6-diisocyanate as the aliphatic polyisocyanate (1).

19. A stable (cyclo) aliphatic polyisocyanate composition as claimed in claim 2, containing 1-isocyanato-3-isocyanatomethyl-3,5,5-trimethylcyclohexane as the cycloaliphatic polyisocyanate (1).

20. A process as claimed in claim 11, wherein
   from 1 to 1000 ppm of at least one primary stabilizer (2a) or
   from 1 to 1000 ppm of at least one secondary stabilizer (2b) or
   from 1 to 1000 ppm of at least one acidic stabilizer (2c) or a stabilizer system comprising
      from 1 to 1000 ppm of (2a),
      from 0 to 1000 ppm of (2b) and
      from 0 to 1000 ppm of (2c)
   is incorporated in the (cyclo) aliphatic polyisocyanate compositions.

21. A stable cycloaliphatic or aliphatic polyisocyanate composition containing
   1) a cycloaliphatic or aliphatic polyisocyanate obtained by thermal cleavage of cycloaliphatic or aliphatic polycarbamates and
   2) a stabilizer selected from the group consisting of
      2a) primary stabilizers selected from the group consisting of sterically hindered phenolic antioxidants, aromatic amines, and mixtures thereof, or 2b) secondary stabilizers selected from the group consisting of peroxide cleaving agents, reducing agents and mixtures thereof, or 2c) acidic stabilizers selected from the group consisting of monocarboxylic acids, organic polycarboxylic acids, Inorganic acids, diester of phosphoric acid, diester of phosphorous acid, acyl chlorides, inorganic acid chlorides and mixtures thereof, wherein at least one primary stabilizer (2a) and at least one acidic stabilizer (2c) are employed.

22. A stable (cyclo)aliphatic polyisocyanate composition as claimed in claim 21, containing, as secondary stabilizers (2b), at least one organic phosphite, at least one thioether or a mixture of at least one organic phosphite and at least one thioether.

23. A stable (cyclo)aliphatic polyisocyanate composition as claimed in claim 21, containing, as acidic stabilizers (2c), at least one organic monocarboxylic acid, at least one organic polycarboxylic acid, at least one Inorganic acid, at least one diester of phosphoric acid or of phosphorous acid, at least one acyl chloride or at least one inorganic acid chloride or a mixture of at least two of the stated acidic stabilizers.

24. A stable (cyclo)aliphatic polyisocyanate composition as claimed in claim 22, containing 2a) from 1 to 1000 ppm of at least one primary stabilizer (2a) or 2b) from 1 to 1000 ppm of at least one secondary stabilizer (2b) or 2c) from 1 to 1000 ppm of at least one acidic stabilizer (2c) or 3) a stabilizer system comprising
from 1 to 1000 ppm of (2a),
from 0 to 1000 ppm of (2b) and
from 0 to 1000 ppm of (2c), the amounts being based on the weight of the polyisocyanate composition.

* * * * *